United States Patent [19]

Drauz et al.

[11] Patent Number: 4,469,876
[45] Date of Patent: Sep. 4, 1984

[54] PROCESS FOR THE PRODUCTION OF L-PROLINE

[75] Inventors: Karlheinz Drauz, Freigericht; Axel Kleemann, Hanau; Jürgen Martens, Alzenua; Paul Scherberich, Constance; Franz Effenberger, Stuttgart, all of Fed. Rep. of Germany

[73] Assignee: Degussa Aktiengesellschaft, Frankfurt, Fed. Rep. of Germany

[21] Appl. No.: 418,841

[22] Filed: Sep. 16, 1982

[30] Foreign Application Priority Data

Sep. 19, 1981 [DE] Fed. Rep. of Germany ....... 3137377

[51] Int. Cl.$^3$ ........................................... C07D 207/12
[52] U.S. Cl. .................................................. 548/535
[58] Field of Search ......................................... 548/535

[56] References Cited

U.S. PATENT DOCUMENTS 3,636,043  1/1972  Magerlein ........................... 548/535

OTHER PUBLICATIONS

Enders, et al., Chem. Bes. 112, pp. 3703—3714, (1979).
Monteiro, Synthesis, Communications, 1974, p. 137.

Primary Examiner—Joseph P. Brust
Attorney, Agent, or Firm—Cushman, Darby & Cushman

[57] ABSTRACT

L-proline is produced from the methyl or ethyl ester of L-pyroglutamic acid by reacting this with at least twice the molar amount of phosgene to form the corresponding 1-chlorocarbonyl-5,5-dichloroproline ester, producing the corresponding 2-chloro-1-chlorocarbonyl-pyrrolin-(2)-carboxylic acid ester-(5) therefrom by splitting off hydrogen chloride, catalytically hydrogenating the pyrrolin-(2) compound to the corresponding N-chlorocarbonyl-proline ester and hydrolyzing the latter with acid to form L-proline.

7 Claims, No Drawings

PROCESS FOR THE PRODUCTION OF L-PROLINE

BACKGROUND OF THE INVENTION

The subject matter of the invention is a new process for the production of L-proline from an L-pyroglutamic acid ester.

There are already known various processes for the production of L-proline from the methyl or ethyl ester of pyroglutamic acid. The known processes, however, produce L-proline only in small yields.

It is also known already to produce L-proline through the reaction of free L-pyroglutamic acid with triethyloxonium-tetrafluoroborate and subsequent reduction of the iminoether obtained with sodium borohydride (Synthesis 1974, page 137). As the yield there is given 75%. Apart from the fact that this yield could not be reproduced by other authors (see e.g. D. Enders et al, in Chem. Ber. Vol. 112, pages 3703-3714, especially page 3714 (1979), footnote 19), the triethyloxonium tetrafluoroborate which is needed in great excess is very difficult to handle so that converting this process to an industrial scale does not appear possible.

SUMMARY OF THE INVENTION

The process of the invention comprises (a) reacting an L-pyroglutamic acid ester of the general formula

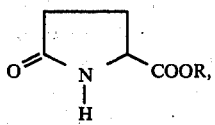

(I)

in which R is a methyl or ethyl group in an inert solvent with at least 2 moles per mole of the compound employed of general formula (I) of phosgene and subsequently separating off the solvent and excess phosgene by distillation, (b) heating the residue obtained in reaction step (a) in an inert solvent with at least 1 mole per mole of the originally employed compound of general formula (I) of an acid acceptor for 3 to 10 hours at a temperature between 60° and 100° C., (c) hydrogenating the crude reaction mixture obtained in reaction step (b) or the compound of the general formula

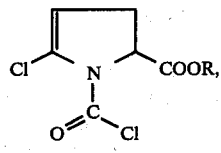

(III)

where R again is either a methyl or ethyl group isolated therefrom by distillation and dissolved in an inert solvent in the presence of a hydrogenation catalyst and at least the stoichiometrical amount of an acid acceptor at a temperature between 0° and 100° C. and a hydrogen pressure between 1 and 300 bar and subsequently separating the hydrogenation catalyst by filtration, (d) hydrolyzing the crude reaction mixture obtained in reaction step (c) or the compound of the general formula

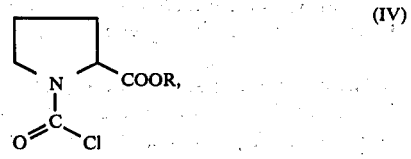

(IV)

in which R again is a methyl or ethyl group isolated therefrom by distillation, with an aqueous mineral acid or a mixture of an aqueous mineral acid and formic acid or acetic acid, and (e) isolating from the hydrolysis mixture obtained in reaction step (d) the L-proline contained therein in known manner.

By the process of the invention the methyl or ethyl ester of L-pyroglutamic acid (pyrrolidone-(2)-carboxylic acid-(5)) can be converted into L-proline easily and in high yields with preservation of the configuration at the asymmetrical carbon atom. Since the methyl and ethyl esters of L-pyroglutamic acid in turn likewise can be produced according to known process easily and in high yield from L-glutamic acid, the process of the invention altogether opens a new, advantageous and economic way for the production of L-proline from L-glutamic acid.

In carrying out the process of the invention in a first process step the L-pyroglutamic acid ester of the general formula (I) serving as starting material is brought to reaction in an inert solvent with at least double, preferably 2.01 to 12 times, especially 2.05 to 3 times the molar amount of phosgene. The reaction suitably takes place at a temperature between −30° and +50° C. Suitable inert solvents for example are halohydrocarbons, e.g. haloalkanes such as dichloromethane, chloroform, carbon tetrachloride or 1,2-dichloroethane, ethers such as di n-propyl ether, diisopropyl ether, methyl tert. butyl ether, tetrahydrofuran or dioxane, carboxylic acid esters such as ethyl acetate, propyl acetate, butyl acetate or ethyl propionate; or aromatic hydrocarbons such as benzene or toluene. Preferably there are used dichloromethane, chloroform, 1,2-dichloroethane or the lower alkyl esters of acetic acid.

The first reaction step for example can be carried out in such manner that there is added liquid (=condensed) phosgene to the solution of pyroglutamic acid present in the reaction vessel. This procedure is advantageously undertaken in the temperature range between −30° and +5° C. The phosgene can either be slowly dosed in or can be added in portions or all at once. After the end of the addition of the phosgene stirring suitably is continued for another hour at a temperature in the range mentioned. Subsequently the reaction mixture is advantageously allowed to stand for a further 3 to 12 hours at room temperature.

In this process there is formed from the pyroglutamic acid ester the corresponding 1-chlorocarbonyl-5,5-dichloro-proline ester of the general formula

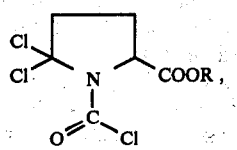

(II)

in which R is a methyl or ethyl group, which can be isolated by careful distillation off of the solvent at low temperature, thus in a given case under reduced pressure.

However, the first reaction step for example, can also be carried out in such manner that there is led into the solution of the pyroglutamic acid ester at a temperature between 5° and 50° C. a strong flow of gaseous phosgene. When the necessary amount of phosgene has been supplied suitably the mixture is stirred for a further 0.5 to 5 hours at the reaction temperature chosen. In this process also there is formed first the corresponding 1-chlorocarbonyl-5,5-dichloroproline ester of the general formula (II). However, because of the higher temperature there can already occur spontaneous splitting off of hydrogen chloride so that a portion of the 1-chlorocarbonyl-5,5-dichloroproline ester is converted into the corresponding 2-chloro-1-chlorocarbonyl-pyrroline-2 carboxylic acid ester-(5) of the general formula (III).

At the end of the first reaction step the solvent and excess phosgene are separated off by distillation. The distillation residue independent of whether it now contains the pure compound of general formula (II) or a mixture of compounds of general formula (II) and (III), is then heated in a second reaction step in an inert solvent with at least 1 mole per mole of originally employed compound of general formula (I) of an acid acceptor for 3 to 10 hours at a temperature between 60° and 100° C., in order to complete the splitting off of hydrogen halide from the compound of general formula (II). Suitable inert solvents are for example the preferably used 1,4-dioxane but there can also be used other ethers such as di n-propyl ether, diisopropyl ether, methyl tert.butyl ether or tetrahydrofuran, carboxylic acid esters such as ethyl acetate, propyl acetate, butyl acetate or ethyl propionate, or aromatic hydrocarbons such as benzene or toluene. Suitable acid acceptors for example are tertiary amines such as triethyl amine, tri-n-propylamine or the especially preferred tri-n-butylamine. If tertiary amines are used as acid acceptors an excess of the tertiary amine can be used as an inert solvent. However, other conventional acid acceptors can be employed. On occasion it can be advantageous to carry out the splitting off of hydrogen chloride in an inert gas atmosphere, e.g. under nitrogen or argon. The pure 2-chloro-1-chlorocarbonyl-pyrroline-(2)-carboxylic acid ester-(5) of general formula (III) can be isolated from the crude reaction mixture of the second reaction step by distillation, suitably under reduced pressure.

The pure compound of general formula (III) or, which is particularly advantageous, the crude reaction mixture of the second step is then subjected to a catalytic hydrogenation in a third reaction step. If the pure compounds of general formula (III) are employed, then they must again be dissolved in an inert solvent. Suitable inert solvents are those already mentioned in the second reaction step. As hydrogenation catalysts generally there are preferred the metals of the 8th side group of the periodic system or suitable compounds of these metals. Typical metals are palladium, rhenium, ruthenium, iridium, and platinum. The metal or metal compounds can be used as such, but also in known manner can be introduced on suitable carriers in the form of carrier catalysts. Especially preferred catalysts are palladium and/or its compounds, such as finely divided palladium metal, especially palladium black, palladium chloride, palladium bromide, palladium iodide, palladium nitrate, palladium oxide or palladium oxide hydrate, or palladium complex salts as tetrachloropalladate or hexachloropalladate, e.g. sodium tetrachloropalladate, sodium hexachloro palladate. Suitable carrier materials for carrier catalysts (i.e. catalysts on carrier) are activated carbon, silica gel, aluminum oxide, zeolites, barium sulfate or calcium carbonate. The hydrogenation catalysts are suitably employed in an amount between 0.01 and 50 weight percent, preferably between 0.1 and 10 weight percent, calculated as active metal and based on the weight of the compound of general formula (III) employed. Insofar as the crude reaction mixture of the second reaction step is directly further processed the amount of catalyst is suitably based on the weight of the compound of general formula (III) theoretically to be expected from the amount originally employed of the compound of general formula (I).

The hydrogenation reaction furthermore requires the presence of an at least stoichiometric amount of an acid acceptor based on the amount employed of the compound of general formula (III). Insofar as the crude reaction mixture of the second reaction step is subjected directly to the hydrogenation suitably, it is again based on the theoretically expected content of the compound of general formula (III). In this case it is furthermore especially advantageous if already before carrying out the second reaction step there is added an amount of acid acceptor which is also sufficient for the third reaction step. In that case especially advantageous is the addition of 2.01 to 10 moles of acid acceptor per mole of compound of general formula (I) originally employed. Suitable acid acceptors are those already mentioned for use in the second reaction step.

The hydrogenation is undertaken in the customary manner for hydrogenations at a temperature between 0° and 100° C., preferably between 25° and 80° C., and a hydrogen pressure between 1 and 300 bar, preferably between 75 and 200 bar. After the end of the hydrogenation the hydrogenation catalyst is separated off from the reaction mixture by filtration.

In the hydrogenation there is formed from the 2-chloro-1-chlorocarbonyl-pyrroline-2-carboxylic acid ester-(5) of general formula (III) the corresponding N-chlorocarbonyl-proline ester of general formula (IV). It can be isolated from the crude reaction mixture by distillation, suitably under reduced pressure.

The compounds of general formula (IV) are new and among other uses represent valuable intermediate products for the production of pesticides or pharmaceuticals (in addition to their use to make proline).

The pure compounds of general formula (IV) or, which again is especially advantageous, the crude reaction mixture of the third reaction step is then hydrolyzed in a fourth reaction step with an aqueous mineral acid or a mixture of an aqueous mineral acid and formic acid or acetic acid. Thus as mineral acids there can be used for example hydrochloric acid, hydrobromic acid, sulfuric acid or phosphoric acid. Preferably there is used aqueous hydrochloric acid or a mixture of aqueous hydrochloric acid and formic acid or acetic acid. If the crude reaction mixture from the third reaction step is subjected directly to hydrolysis then it is suitable if this content of excess acid acceptor is as small as possible. The hydrolysis takes place in the customary manner for hydrolysis with an excess of hydrolysis agent at a temperature between 50° C. and the reflux temperature of the reaction mixture. Generally it requires a reaction time between 1 and 12 hours. Under some circumstances it is advantageous to allow the hydrolysis mixture to stand subsequently for some time, for example 5 hours, at room temperature.

In the hydrolysis simultaneously the chlorocarbonyl group is split off and the ester group saponified from the compound employed of general formula (IV) so that L-proline is formed which is present in the crude hydrolysis mixture as an addition salt of the mineral acid employed and can be isolated from the mixture in known manner, e.g. by means of an ion exchange resin.

The process can comprise, consist essentially of, or consist of the stated steps with the materials set forth.

In the following examples the process of the invention is explained in more detail. Unless otherwise indicated the percentages are by weight.

EXAMPLE 1

35.8 grams of L-pyroglutamic acid methyl ester were dissolved in 300 ml of methylene chloride and cooled to $-10°$ C. There were condensed in a calibrated, cooled dropping funnel 74.8 grams of phosgene. The liquid phosgene was added all at once to the reaction mixture with stirring and exclusion of moisture, stirring continued for 1 hour at $-10°$ C. and the mixture subsequently allowed to stand for 12 hours at room temperature.

After evaporation of the solvent and the excess phosgene the residue was dissolved in 300 ml of dioxane and treated with 110 grams of tri-n-butylamine. This reaction mixture was held in a nitrogen atmosphere under stirring for 3 hours at 75° C.

The clear solution was subsequently hydrogenated in a Hastelloy stirring autoclave with addition of 32 grams of palladium on activated carbon (10%) at 50° C. and a hydrogen pressure of 150 bar until complete uptake of hydrogen. After filtering off the catalyst the crude reaction mixture was added with vigorous stirring to 600 ml of a 75° C. warm, quarter concentrated hydrochloric acid. After the end of the development of gas stirring was continued for a further 3 hours at 75° C. The solution was made alkaline with sodium hydroxide, the tri-n-butylamine separated off and after clarification with activated carbon the aqueous phase evaporated. The residue was taken up in dilute hydrochloric acid, clarified again with activated carbon, evaporated and the residue converted into proline with the help of the basic ion exchanger MP 62. There were obtained 24.3 grams (84.5%) of L-proline having a melting point of 227°–231° C. (decomposition)—$\alpha_D^{20} = -83.6°$ (C=1, H$_2$O).

EXAMPLE 2

There was led into 22.5 grams of L-pyroglutamic acid ethyl ester dissolved in 150 ml of methylene chloride at 45° C. during 3 hours a vigorous stream of phosgene. Then the reaction mixture was allowed to stand a further 3 hours at room temperature.

After evaporating off the solvent the residue was heated in 300 ml of tri-n-butylamine for 3 hours at 70° C. and this reaction mixture hydrogenated with addition of 17 grams of palladium on activated carbon (10%) at 50° C. and a hydrogen pressure of 180 bar in the autoclave until complete reaction.

After hydrolysis and working up as in Example 1 there were obtained 12.8 grams (78%) of L-proline having a melting point of 228°–230° C. (decomposition).

EXAMPLE 3

30.0 grams of L-pyroglutamic acid methyl ester were dissolved in 210 ml of methylene chloride and reacted with 60.0 grams of phosgene according to Example 1.

After evaporation of the solvent and the excess phosgene there was obtained a 54.0 gram residue. A small sample of this residue was recrystallized from diisopropyl ether for characterization and proven to be L-1-chlorocarbonyl-5,5-dichloroproline methyl ester having a melting point of 76°–78° C.

This new compound furnished a correct elemental analysis:

|  | $C_7H_8Cl_3NO_3$ (260.5) | | | |
| --- | --- | --- | --- | --- |
|  | C | H | Cl | N |
| Calculated: | 32.37% | 3.10% | 40.83% | 5.38% |
| Found: | 32.48% | 3.17% | 40.56% | 5.55% |

Likewise the NMR and IR spectra are in agreement with this structure.

EXAMPLE 4

52.1 grams of the residue obtained in Example 3 was stirred for 5 hours at 80° C. with 21.5 grams of triethylamine in 500 ml of dioxane. The reaction was carried out under a nitrogen atmosphere. After the end of the reaction the solid triethylamine hydrochloride was filtered off with reaction, the dioxane removed and the residue fractioned in a vacuum.

There passed over at 0.013 mbar and 110°–118° C. 41.2 grams (92%) of L-2-chloro-1-chlorocarbonyl-pyrroline-(2)-carboxylic acid methyl ester-(5).

This new compound furnished correct IR and NMR spectra.

|  | $C_7H_7Cl_2NO_3$ (224.04) | | | |
| --- | --- | --- | --- | --- |
|  | C | H | Cl | N |
| Calculated: | 37.53% | 3.15% | 31.65% | 6.25% |
| Found: | 37.75% | 3.01% | 31.78% | 6.34% |

EXAMPLE 5

35.8 grams of the L-2-chloro-1-chlorocarbonylpyrroline-2-carboxylic acid methyl ester-(5) isolated in Example 4 were dissolved in 200 ml of dioxane and after addition of 30 grams of tri-n-butylamine and 18.5 grams of palladium on activated carbon (10%) hydrogenated at 50° C. and 125 bar of hydrogen pressure until complete uptake of hydrogen. After separation of the catalyst, the ammonium salt, the solvent and the excess tri-n-butylamine the residue is fractionated in a vacuum.

There is obtained 24.2 grams (79%) of L-N-chlorocarbonylproline methyl ester having a boiling point of 90°–95° C. at 0.013 mbar.

Correct IR and NMR spectra were obtained from this new compound.

|  | $C_7H_{10}Cl\,NO_3$ (191,62) | | | |
| --- | --- | --- | --- | --- |
|  | C | H | Cl | N |
| Calculated: | 43.88% | 5.26% | 18.50% | 7.31% |

-continued

| C7H10Cl NO3 (191,62) | | | |
|---|---|---|---|
| C | H | Cl | N |
| Found: 44.16% | 5.46% | 17.93% | 7.38% |

EXAMPLE 6

19.2 grams of the L-N-chlorocarbonyl-proline methyl ester isolated in Example 5 were dropped with vigorous stirring into 200 ml of a quarter concentrated hydrochloric acid preheated to 75° C. After the end of the development of gas stirring was continued for 1 hour at 75° C. and the mixture allowed to stand for 5 hours at room temperature. The hydrochloric acid solution was evaporated and the residue dehydrohalogenated by means of the weakly basic ion exchanger MP 62. After evaporation of the eluate there were obtained 11.2 grams (97.4% of L-proline having a melting point of 222°–229° C. (decomposition)), $\alpha_D^{20} = -83.6$ (c=1, H$_2$O).

EXAMPLE 7

50 grams of L-pyroglutamic acid ethyl ester were dissolved in 350 ml of methylene chloride and reacted at −10° C. according to Example 1 with 95 grams of phosgene. The solvent and excess phosgene were evaporated under reduced pressure without an increase of the temperature above 30° C.

A small sample of the residue obtained proved to be pure L-1-chlorocarbonyl-5,5-dichloroproline ethyl ester according to the NMR and IR spectra.

| C8H10Cl3NO3 (274,53) | | | |
|---|---|---|---|
| C | H | Cl | N |
| Calculated: 35.00% | 3.67% | 38.74% | 5.10% |
| Found: 35.24% | 3.60% | 38.72% | 5.07% |

EXAMPLE 8

87.2 grams of the residue obtained in Example 7 were reacted according to Example 4 with 40 grams of triethylamine in 500 ml of dioxane. After working up there were obtained by distillation 61.3 grams (81%) of L-2-chloro-1-chlorocarbonylpyrroline-(2)-carboxylic acid ethyl ester-(5) having a boiling point of 120°–124° C. at a pressure of 0.06 mbar.

This new compound produced correct IR and NMR spectra and gave agreeing elemental analytical data

| C8H9Cl2NO3 (238,07) | | | |
|---|---|---|---|
| C | H | Cl | N |
| Calculated: 40.36% | 3.31% | 29.78% | 5.88% |
| Found: 40.56% | 2.89% | 29.50% | 5.91% |

EXAMPLE 9

45.0 grams of L-pyroglutamic acid ethyl ester were dissolved in 300 ml of methylene chloride and at 45° C. there was led in during 3 hours a vigorous flow of phosgene. After the end of the reaction stirring was continued for a further 3 hours at 45° C. After evaporation of the solvent there was obtained as residue a colorless oil whose composition was determined by NMR spectroscopy to be about 70% L-1-chlorocarbonyl-5,5-dichloroproline methyl ester and 30% L-2-chloro-1-chlorocarbonylpyrroline-(2)-carboxylic acid ethyl ester-(5).

The oil was dissolved in 400 ml of dioxane and after addition of 32 grams of triethylamine held with stirring for 5 hours at 75° C. under a nitrogen atmosphere. After the end of the reaction the triethylamine hydrochloride was filtered off with suction, the filtrate evaporated and the residue fractionated in a vacuum.

There passed over at a pressure of 0.06 mbar 53.8 grams (79%) of L-2-chloro-1-chlorocarbonylpyrroline-(2)-carboxylic acid ethyl ester-(5) at 120°–124° C.

EXAMPLE 10

47.6 grams of the L-2-chloro-1-chlorocarbonylpyrroline-(2)-carboxylic acid ethyl ester-(5) isolated in Example 8 or 9 was hydrogenated according to Example 5 at a hydrogen pressure of 180 mbar. After distillation there were obtained 30.0 grams (73%) of L-N-chloro-carbonyl-proline ethyl ester having a boiling point of 90° C. at 0.001 mbar. This new compound was characterized by spectroscopic and elemental analytical data:

| C8H12Cl NO3 (205,64) | | | |
|---|---|---|---|
| C | H | Cl | N |
| Calculated: 47.73% | 5.88% | 17.24% | 6.81% |
| Found: 46.80% | 6.03% | 17.20% | 7,21% |

EXAMPLE 11

20.6 grams of the L-N-chlorocarbonyl-proline ethyl ester isolated in Example 10 were reacted according to Example 6 with aqueous hydrochloric acid. After working up there were obtained 11.3 grams (98.2%) of L-proline having a melting point of 224°–230° C. (decomposition), $\alpha_D^{20} = -83.7\%$ (c=1, H$_2$O).

What is claimed is:

1. A process for the production of L-proline from an L-pyroglutamic acid ester comprising
   (a) reacting an L-pyroglutamic acid ester of the formula

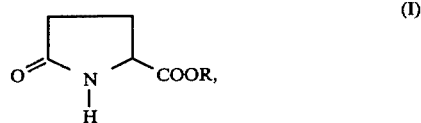

(I)

in which R is a methyl or ethyl group in an inert solvent with 2 to 12 moles per mole of the compound employed of formula (I) of phosgene at a temperature of −30° to +50° C. and subsequently separating off the solvent and excess phosgene by distillation,
   (b) heating the residue obtained in reaction step (a) in an inert solvent with at least 1 mole per mole of the originally employed compound of general formula (I) of a tertiary amine as an acid acceptor for 3 to 10 hours at a temperature between 60° and 100° C.,
   (c) hydrogenating either (1) the crude reaction mixture obtained in reaction step (b) or (2) the compound of formula

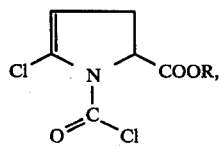

(III)

isolated therefrom by distillation and dissolved in an inert solvent, in the presence of a metal of the eighth side group of the periodic system or a compound of such a metal as a hydrogenation catalyst and at least the stoichiometrical amount of a tertiary amine as an acid acceptor at a temperature between 0° and 100° C. and a hydrogen pressure between 1 and 300 bar and subsequently separating the hydrogenation catalyst by filtration, (d) hydrolyzing either (1) the crude reaction mixture obtained in reaction step (c) or (2) the compound of formula

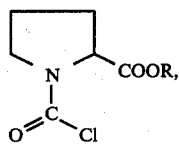

(IV)

isolated therefrom by distillation, with an aqueous mineral acid or a mixture of an aqueous mineral acid and formic acid or acetic acid at a temperature between 50° C. and the reflux temperature, and (e) isolating from the hydrolysis mixture obtained in reaction step (d) the L-proline contained therein.

2. A process according to claim 1 wherein reaction step (a) is carried out at a temperature between −30° and +5° C. and the phosgene is added in condensed form.

3. A process according to claim 1 wherein reaction step (a) is carried out at a temperature between 5° and 50° C. and phosgene is led in as a gas.

4. A process according to claim 1 wherein in reaction step (d) there is employed as the hydrolysis medium aqueous hydrochloric acid or a mixture of aqueous hydrochloric acid with either formic acid or acetic acid.

5. A process according to claim 1 wherein there is employed in step (c) the crude reaction mixture obtained in reaction step (b) and there is employed in reaction step (d) the crude reaction mixture obtained in reaction step (c).

6. A process according to claim 1 wherein step (b) is carried out in an inert atmosphere.

7. A process according to claim 1 wherein in step (a) the solvent is a halohydrocarbon, an ether, an ester of a carboxylic acid, or an aromatic hydrocarbon, step (b) is carried out in an ether, an ester of a carboxylic acid, or an aromatic hydrcarbon, and step (c) is carried out in an ether, an ester of a carboxylic acid, or an aromatic hydrocarbon.

* * * * *